(12) United States Patent
Seiler et al.

(10) Patent No.: US 12,329,415 B2
(45) Date of Patent: Jun. 17, 2025

(54) SPINAL ROD WITH MULTIPLE SECTIONS HAVING ECCENTRIC CENTERS

(71) Applicant: Warsaw Orthopedic, Inc., Warsaw, IN (US)

(72) Inventors: Michael J. Seiler, Charlottesville, VA (US); Rex W. Armstrong, Cordova, TN (US)

(73) Assignee: WARSAW ORTHOPEDIC, INC., Warsaw, IN (US)

( * ) Notice: Subject to any disclaimer, the term of this patent is extended or adjusted under 35 U.S.C. 154(b) by 0 days.

(21) Appl. No.: 18/163,969

(22) Filed: Feb. 3, 2023

(65) Prior Publication Data

US 2024/0260994 A1 Aug. 8, 2024

(51) Int. Cl.
*A61B 17/56* (2006.01)
*A61B 17/70* (2006.01)

(52) U.S. Cl.
CPC ........ *A61B 17/56* (2013.01); *A61B 2017/564* (2013.01); *A61B 17/7002* (2013.01)

(58) Field of Classification Search
CPC ............ A61B 17/7004; A61B 17/7005; A61B 17/701; A61B 17/7011
See application file for complete search history.

(56) References Cited

U.S. PATENT DOCUMENTS

| | | | |
|---|---|---|---|
| 5,217,461 A | 6/1993 | Asher et al. | |
| 8,118,840 B2 * | 2/2012 | Trieu | A61B 17/7031 606/254 |
| 8,657,856 B2 | 2/2014 | Gephart et al. | |
| 9,011,494 B2 * | 4/2015 | Trieu | A61B 17/7031 606/254 |
| 9,101,400 B2 | 8/2015 | Trieu et al. | |
| 9,232,964 B2 * | 1/2016 | Freudiger | A61B 17/7004 |
| 11,160,583 B2 | 11/2021 | Lee et al. | |
| 2005/0065516 A1 * | 3/2005 | Jahng | A61B 17/7028 606/259 |
| 2007/0191846 A1 * | 8/2007 | Bruneau | A61B 17/7008 606/86 A |

(Continued)

OTHER PUBLICATIONS

International Search Report and Written Opinion in Application No. PCT/IB2024/050950 dated Apr. 26, 2024.

*Primary Examiner* — Ellen C Hammond
*Assistant Examiner* — Holly Joanna Lane
(74) *Attorney, Agent, or Firm* — FOX ROTHSCHILD LLP

(57) ABSTRACT

A spinal rod with multiple sections having eccentric centers for use in a spinal fixation device is disclosed. The spinal rod may include a first longitudinal portion and a second longitudinal portion adjoined together by a transition portion. The first longitudinal portion may extend along a first longitudinal axis that extends lengthwise through a center of the first longitudinal portion and the second longitudinal portion may extend along a second longitudinal axis that extends lengthwise through a center of the second longitudinal portion. The transition portion may be configured to transition from the first cross-section to the second cross-section such that the first longitudinal axis is offset with respect to the second longitudinal axis. In at least some embodiments, a first outside surface of the first longitudinal portion may extend along a co-extensive plane with a second outside surface of the second longitudinal portion.

20 Claims, 12 Drawing Sheets

(56) References Cited

U.S. PATENT DOCUMENTS

| | | |
|---|---|---|
| 2008/0021461 A1 | 1/2008 | Barker et al. |
| 2008/0177320 A1* | 7/2008 | McBride ............ A61B 17/7004 606/261 |
| 2010/0114165 A1* | 5/2010 | Ely .................... A61B 17/7004 606/264 |
| 2011/0060365 A1* | 3/2011 | Felix .................. A61B 17/7011 606/264 |
| 2012/0290013 A1* | 11/2012 | Simonson .......... A61B 17/7004 606/279 |
| 2014/0257393 A1* | 9/2014 | Trieu ................. A61B 17/7004 606/279 |
| 2016/0120575 A1 | 5/2016 | Barrus |
| 2018/0168694 A1* | 6/2018 | Lee .................... A61B 17/7011 |
| 2019/0374257 A1* | 12/2019 | Bedor ................ A61B 17/7004 |
| 2020/0000495 A1 | 1/2020 | Italiaie et al. |
| 2021/0137564 A1 | 5/2021 | Sharifi-Mehr et al. |

\* cited by examiner

100

100

100

100

100

101

101

101

101

101

SPINAL ROD WITH MULTIPLE SECTIONS HAVING ECCENTRIC CENTERS

FIELD

The present disclosure generally relates to medical devices for the treatment of musculoskeletal disorders, and more particularly to a vertebral rod, which provides stability while reducing stress on spinal elements.

BACKGROUND

Spinal disorders such as degenerative disc disease, disc herniation, osteoporosis, spondylolisthesis, stenosis, scoliosis and other curvature abnormalities, kyphosis, tumor, and fracture may result from factors including trauma, disease and degenerative conditions caused by injury and aging. Spinal disorders typically result in symptoms including pain, nerve damage, and partial or complete loss of mobility.

Non-surgical treatments, such as medication, rehabilitation and exercise may be effective, however, they may fail to relieve the symptoms associated with these disorders. Surgical treatment of these spinal disorders includes discectomy, laminectomy, fusion and implantable prosthetics. As part of these surgical treatments, connecting elements such as vertebral rods are often used to provide stability to a treated region. During surgical treatment, one or more rods may be attached to the exterior of two or more vertebral members.

Longitudinal rods may redirect stresses away from a damaged or defective region while healing takes place to restore proper alignment and generally support the vertebral members. In some applications, longitudinal rods may be attached to the vertebral members via a pedicle screw and/or tulip head type connector without the use of implants or spinal fusion. At least one problem occurring in the relevant art field may occur when a longitudinal rod spans the cervical spine and the thoracic spine, e.g., the cervico-thoracic junction at the C7 and T1 vertebrae. Due to the different screw sizes utilized for cervical vertebrae and thoracic vertebrae and the anatomical differences at the transition area, i.e., junction between the thoracic spine and the cervical spine, it is often not possible to optimally secure a pedicle screw at the junction area to the longitudinal rod, even after bending the longitudinal rod, because current longitudinal rods may be difficult to adjust to adequately conform with the natural dorsal height difference between vertebrae in this area. This may result in what is known in the art field as a "missed level." In conventional applications, a contoured rod with concentric centers is utilized. While such contoured rod may provide adequate structure that can conform with the natural spine shape in other areas of the spine, the contoured rod with concentric centers may require surgeons to skip placing a screw at the cervico-thoracic junction.

In another application, a surgeon may employ two separate longitudinal rods each aligned at the thoracic spine and the cervical spine joined by a connector at the thoracic spine and cervical spine transition. This introduces additional problems such as lack of flexibility throughout the longitudinal rod and potential inability to connect the longitudinal rod to a pedicle screw at the cervico-thoracic junction. While prior vertebral rods have attempted to provide effective spinal stabilization, there remains a need for a longitudinal rod that provides a stable support by that allows for connecting it to a pedicle screw at the thoracic spine and cervical spine transition, while maintaining the flexibility of the longitudinal rod throughout the spinal column. Therefore, there exists a need to provide a solution in which a longitudinal rod can effectively and more easily secure multiple vertebral levels and span the transition area where the thoracic spine becomes the cervical spine without skipping a vertebral level.

SUMMARY

The techniques of this disclosure generally relate to spinal rods with multiple sections, i.e., cross sections, having eccentric centers. In various embodiments, these spinal rods may be broadly understood as a multi-diameter rod with multiple sections having eccentric centers. Disclosed embodiments may be configured for use in a spinal surgery that may enable a surgeon to securely couple the rod to the corresponding vertebrae of a cervico-thoracic junction of the human spine. Similarly, disclosed embodiments may also be useful in a spinal surgery spanning the vertebrae of the lumbar-thoracic junction of the human spine.

In one aspect, the present disclosure provides for a spinal rod for use in spinal surgery. In various embodiments, the spinal rod may include a first longitudinal portion extending along a first longitudinal axis and having a first cross-section and a first end portion, and the first longitudinal axis may extend lengthwise through a center of the first longitudinal portion. The example spinal rod may include a second longitudinal portion extending along a second longitudinal axis having a second cross-section and a second end portion opposite the first end portion, and the second longitudinal axis may extend lengthwise through a center of the second longitudinal portion. The example spinal rod may include a transition portion adjoining the first longitudinal portion and the second longitudinal portion that is configured to transition from the first cross-section to the second cross-section such that the first longitudinal axis is offset with respect to the second longitudinal axis. In at least some embodiments, a first outside surface of the first longitudinal portion extends from the first end portion and towards the second end portion along a co-extensive plane with a second outside surface of the second longitudinal portion that extends from the second end portion and towards the first end portion.

In another aspect, the present disclosure provides a method for treating a plurality of vertebrae regions in a patient. In various embodiments, the method may include providing the spinal rod, then attaching the spinal rod to the first plurality of bone anchors, e.g., pedicle screws and/or lateral mass screws in the thoracic region of the spine and a second plurality of bone anchors, e.g., pedicle screws or lateral mass screws in the cervical region of the spine. The example method may include aligning the transition portion of the spinal rod above a cervico-thoracic junction such that the first longitudinal portion spans and supports the thoracic region of the spine and the second longitudinal portion spans and supports the cervical region of the spine.

In another aspect, the present disclosure provides for a system including a spinal rod, for use in a spinal surgery. In various embodiments, the system may include a first plurality of bone anchors, e.g., pedicle screws or lateral mass screws, configured for attachment to the cervical spine, and a second plurality of bone anchors, e.g., pedicle screws, configured for attachment to the thoracic spine. The example spinal surgery system may include a first longitudinal portion of the spinal rod extending along a first longitudinal axis and having a first cross-section and a first end portion. In some embodiments, the first longitudinal axis may extend lengthwise through a center of the first longitudinal portion.

In at least some embodiments, the spinal surgery system may include a second longitudinal portion extending along a second longitudinal axis and having a second cross-section and a second end portion. In various embodiments, the second longitudinal axis may extend lengthwise through a center of the second longitudinal portion. In at least some embodiments, the surgery system may include a transition portion adjoining the first longitudinal portion and the second longitudinal portion that may be configured to transition from the first cross-section to the second cross-section such that the first longitudinal axis may be offset with respect to the second longitudinal axis. In some embodiments, a first outside surface of the first longitudinal portion that extends from the first end portion and towards the second end portion may extend along a co-extensive plane with a second outside surface of the second longitudinal portion. In various embodiments, the second outside surface of the second longitudinal portion may extend from the second end portion and towards the first end portion. In at least some embodiments, the first longitudinal portion may be configured to connect to the first plurality of pedicle screws and the second longitudinal portion may be configured to connect to the second plurality of pedicle screws or lateral mass screws such that each vertebrae adjacent the transition portion is connected to the spinal rod.

The details of one or more aspects of the disclosure are set forth in the accompanying drawings and the description below. Other features, objects, and advantages of the techniques described in this disclosure will be apparent from the description and drawings, and from the claims.

DETAILED DESCRIPTION

Figure 1:
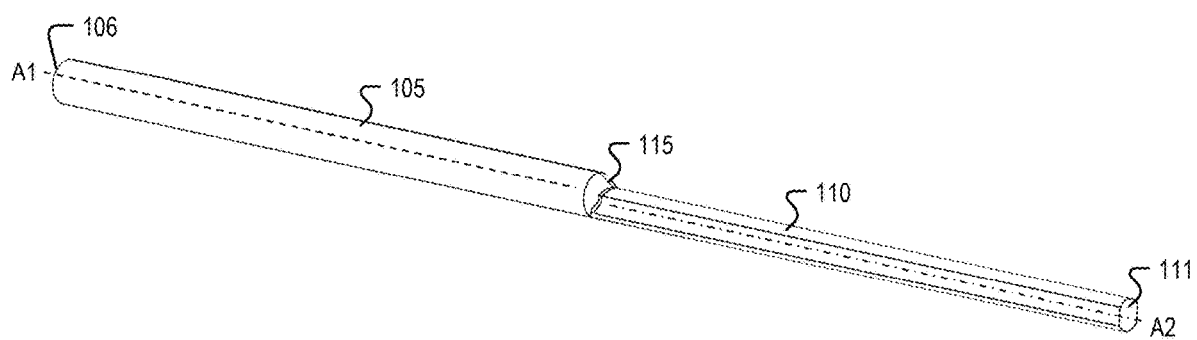
FIG. 1 depicts a perspective view of a first embodiment of a spinal rod with eccentric centers.
Figure 2A:
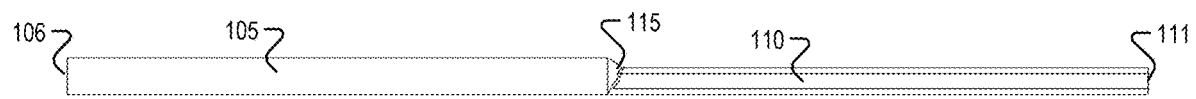
FIG. 2A depicts a side view of the spinal rod shown in FIG. 1.
Figure 2B:
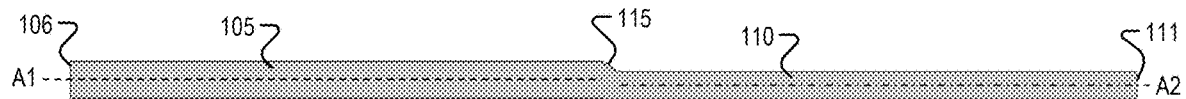
FIG. 2B depicts a cross-sectional side view through the length of the spinal rod shown in FIG. 1.

Embodiments of the present disclosure relate generally, for example, to spinal stabilization systems, and more particularly, to surgical instruments for use with spinal stabilization systems. Embodiments of the devices and methods are described below with reference to the Figures.

The following discussion omits or only briefly describes certain components, features and functionality related to medical implants, installation tools, and associated surgical techniques, which are apparent to those of ordinary skill in the art. It is noted that various embodiments are described in detail with reference to the drawings, in which like reference numerals represent like parts and assemblies throughout the several views, where possible. Reference to various embodiments does not limit the scope of the claims appended hereto because the embodiments are examples of the inventive concepts described herein. Additionally, any example(s) set forth in this specification are intended to be non-limiting and set forth some of the many possible embodiments applicable to the appended claims. Further, particular features described herein may be used in combination with other described features in each of the various possible combinations and permutations unless the context or other statements clearly indicate otherwise.

Terms such as "parallel," "transverse," "longitudinal," "axial," etc. as used herein are intended to encompass a meaning of exactly the same while also including variations that may occur, for example, due to manufacturing processes. The term "substantially" may be used herein to emphasize this meaning, particularly when the described embodiment has the same or nearly the same functionality or characteristic, unless the context or other statements clearly indicate otherwise. The term "about" may also be used herein to emphasize this meaning and if a value and/or a range of values is provided in the specification or claims with the modifier "about" a meaning of +/− ten percent (10%) to those provided values are encompassed by the meaning of "about," unless the context clearly indicates otherwise.

Further, as used in the specification and including the appended claims, "treating" or "treatment" of a disease or condition refers to performing a procedure that may include administering one or more drugs to a patient (human, normal or otherwise or other mammal), in an effort to alleviate signs or symptoms of the disease or condition. Alleviation can occur prior to signs or symptoms of the disease or condition appearing, as well as after their appearance. Thus, treating or treatment includes preventing or prevention of disease or undesirable condition (e.g., preventing the disease from occurring in a patient, who may be predisposed to the disease but has not yet been diagnosed as having it). In addition, treating or treatment does not require complete alleviation of signs or symptoms, does not require a cure, and specifically includes procedures that have only a marginal effect on the patient. Treatment can include inhibiting the disease, e.g., arresting its development, or relieving the disease, e.g., causing regression of the disease. For example, treatment can include reducing acute or chronic inflammation: alleviating pain and mitigating and inducing re-growth of new ligament, bone and other tissues: as an adjunct in surgery; and/or any repair procedure. Also, as used in the specification and including the appended claims, the term "tissue" includes soft tissue, ligaments, tendons, cartilage and/or bone unless specifically referred to otherwise.

Furthermore, as used herein, it is understood that the term "sagittal plane" includes any plane of section in the anatomical position that generally passes vertically through the human body in the prone position, is generally perpendicular to both the coronal plane and the horizontal (or axial or transverse) plane, generally dividing the human body into left and right sections, and further includes any plane of section in the anatomical position that generally passes vertically through the human body in the prone position, is generally perpendicular to the horizontal (or axial or transverse) plane, and is generally angularly oriented from the coronal plane at an angle of orientation ranging from greater than zero degrees up to and including ninety degrees.

Spatially relative terms such as "below;" "lower," "upper," "side," "front," and the like, are used for ease of description to explain the positioning of one element relative to a second element. These terms are intended to encompass different orientations of the device in addition to different orientations than those depicted in the figures. Further, terms such as "first," "second," and the like, are also used to describe various elements, regions, sections, portions and are also not intended to be limiting. Like terms refer to like elements throughout the description.

As used herein, the terms "having," "containing," "including." "comprising," and the like are open ended terms that indicate the presence of stated elements or features, but do not preclude additional elements or features. The articles "a," "an," and "the," are intended to include the plural as well as the singular unless the context clearly indicates otherwise.

Figure 13:
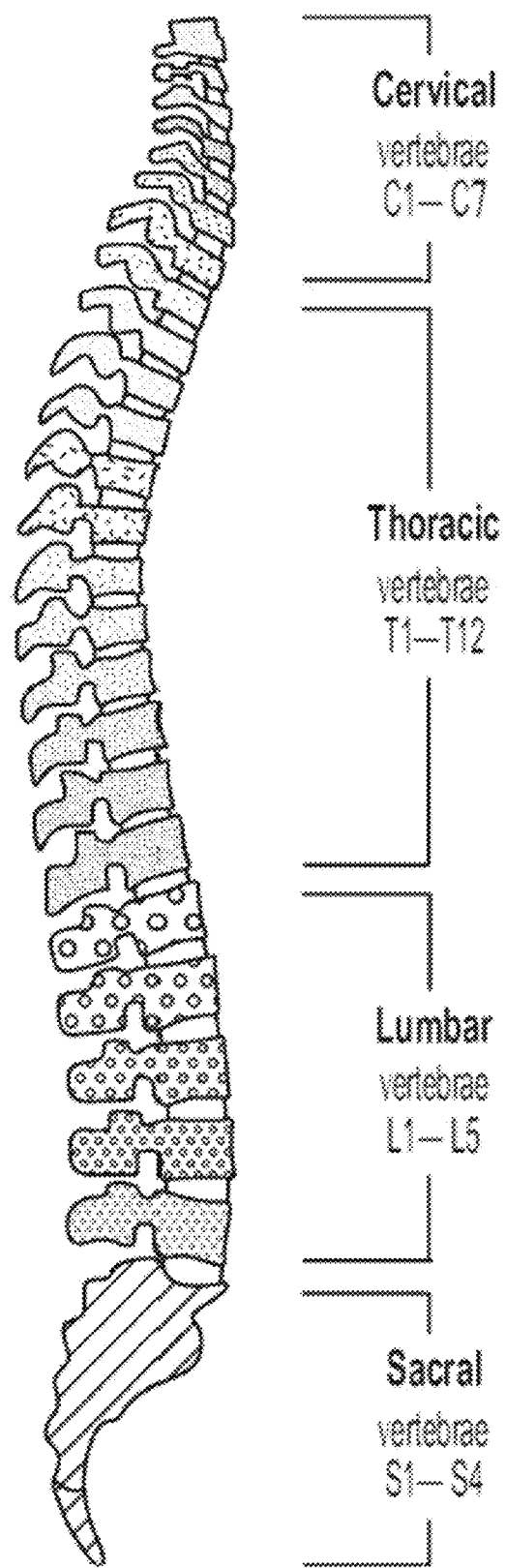
FIG. 13 depicts a reference diagram of various anatomical planes of the human body.

Before discussing the details of the relevant disclosed embodiments, it is helpful to briefly discuss the relevant human anatomy. The human spine, as depicted in FIG. 13, consists of a stack of 33 curved vertebrae that are structurally divided into five regions, namely, cervical region (C1-C7), thoracic region (T1-T12), lumbar region (L1-L5) and, the fused sacrum and coccyx regions. Towards the bottom of the spine, the vertebrae are larger because the spine supports heavier loads of the body in this area. The cervical vertebrae, forming the neck area, are relatively small to promote flexibility of the head and because they support smaller loads relative to the thoracic and lumbar regions. Just below the cervical vertebrae are the thoracic vertebrae, which form the upper back. The thoracic vertebrae are larger than the cervical vertebrae and increase in size from top towards bottom. Below the thoracic region lies the lumbar vertebrae, which are even larger and support the weight of the entire upper body. Relative motion in the spine may also vary along the length of the spinal column, as the cervical vertebra have a greater range of motion than the lower lumbar vertebra.

Figure 11:
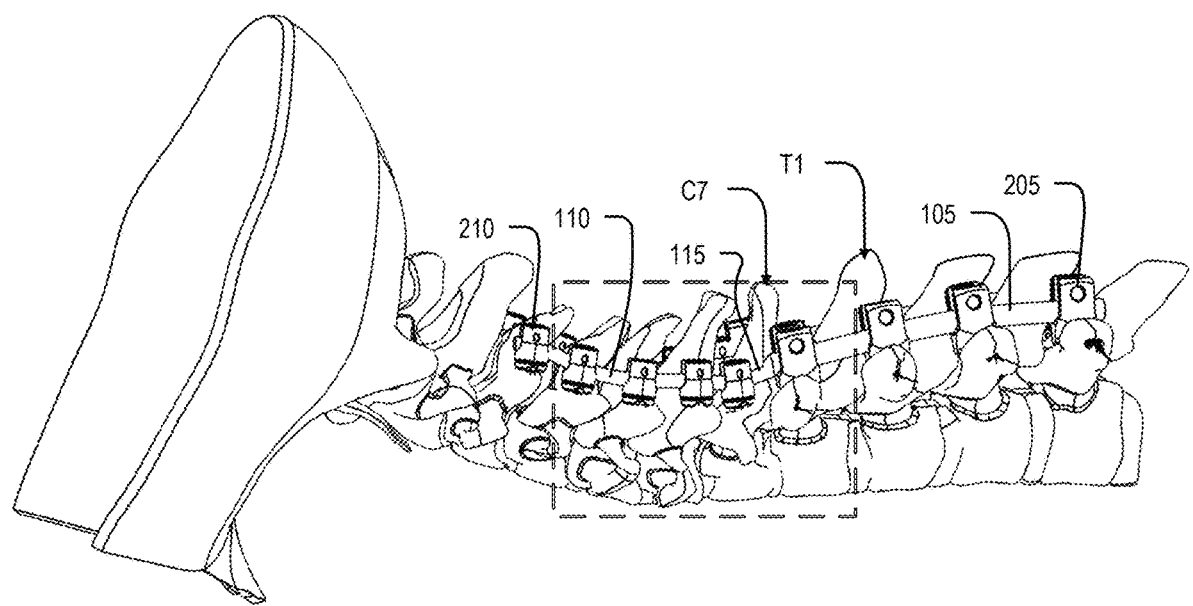
FIG. 11 depicts an installed spinal rod connected to the cervical spine and the thoracic spine by a plurality of differently sized stabilizing pedicle screw assemblies.
Figure 12:
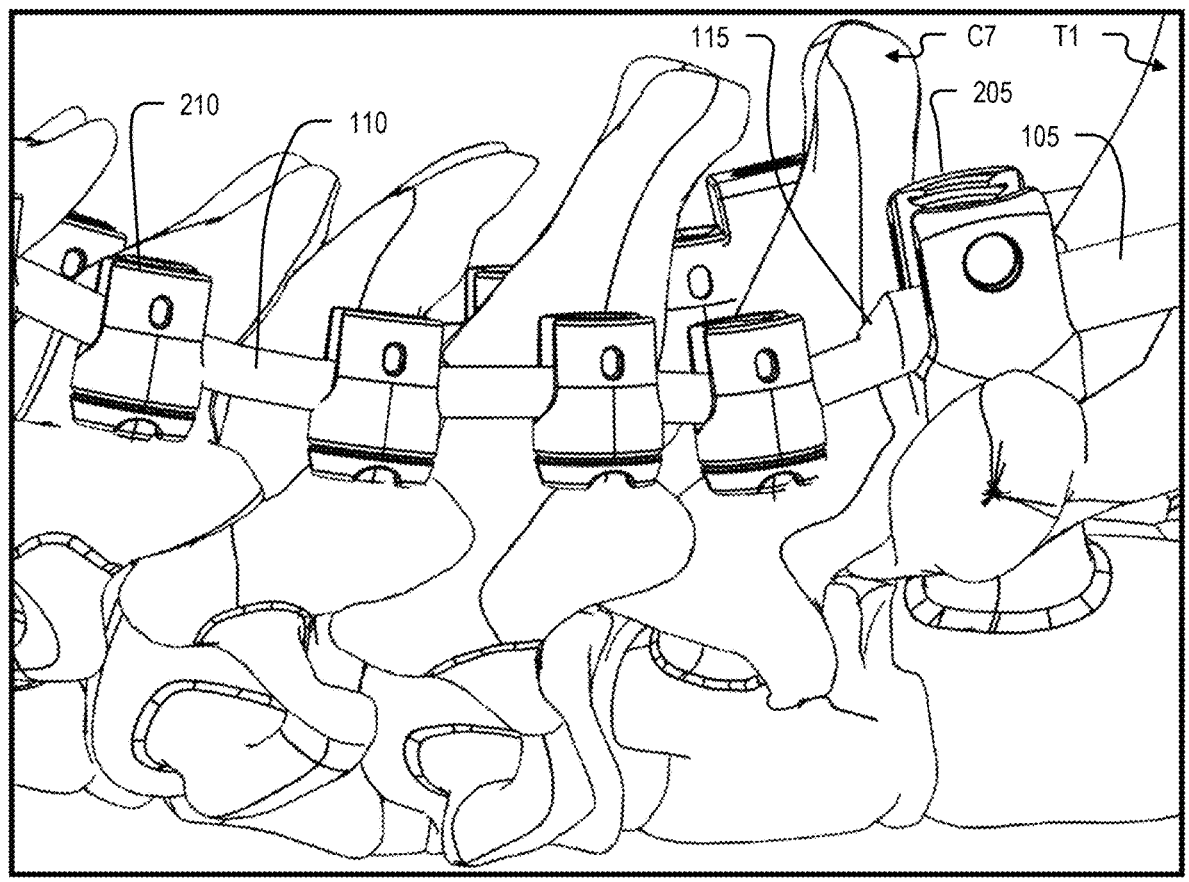
FIG. 12 depicts an enlarged view of a cervico-thoracic junction area shown in FIG. 11.

As shown in FIGS. 11 and 12, due to the natural curvature of the spine, there is a dorsal height difference between the cervical and thoracic vertebrae that forms the cervico-thoracic junction at the C7 and T1 vertebrae transition. Disclosed embodiments are designed and/or optimized to ensure that the cervico-thoracic junction may be properly supported by a longitudinal rod spanning at least a portion of the cervical spine and the thoracic spine.

The following discussion includes a description of a muti-diameter rod or a longitudinal rod and/or vertebral rod, with eccentric centers, related components and exemplary methods of employing the spinal rod in accordance with the principles of the present disclosure. Alternate embodiments are also disclosed. Reference will now be made in detail to the exemplary embodiments of the present disclosure, which are illustrated in the accompanying figures.

The various spinal rod embodiments disclosed herein may include first and second elongated member portions with eccentric centers that may be contoured to more closely resemble the natural structure of the curvature of the spine, e.g., by having a smaller diameter portion oriented higher along the spinal column towards the cervical vertebrae. As briefly mentioned above, disclosed multi-diameter eccentric rod embodiments may reduce the height of the smaller diameter member in relation to the larger diameter member allowing for an effective multiple level procedure without skipping a vertebral level at the cervico-thoracic junction.

FIGS. 1-10 illustrate various embodiments of a multi-diameter rod 100, 101 with eccentric centers in accordance with the principles of the present disclosure. Like reference numerals indicate similar parts throughout the figures. It is to be understood that the figures are not drawn to scale. Further, the relation between objects in a figure may not be to scale and may in fact have a reverse relationship as to size. The figures are intended to bring understanding and clarity to the structure of each object shown, and thus, some features may be exaggerated in order to illustrate a specific feature of a structure.

Components of the disclosed embodiments may be fabricated from biologically acceptable materials suitable for medical applications, including metals, synthetic polymers, ceramics and bone material and/or their composites. For example, the components, individually or collectively, may be fabricated from materials such as stainless steel alloys, commercially pure titanium, titanium alloys, Grade 5 titanium, super-elastic titanium alloys, cobalt-chrome alloys, superelastic metallic alloys (e.g., Nitinol, super elasto-plastic metals, such as GUM METAL®), ceramics and composites thereof such as calcium phosphate (e.g., SKELITE™), thermoplastics such as polyaryletherketone (PAEK) including polyetheretherketone (PEEK), polyetherketoneketone (PEKK) and polyetherketone (PEK), carbon-PEEK composites, PEEK-$BaSO_4$ polymeric rubbers, polyethylene terephthalate (PET), fabric, silicone, polyurethane, silicone-polyurethane copolymers, polymeric rubbers, polyolefin rubbers, hydrogels, semi-rigid and rigid materials, elastomers, rubbers, thermoplastic elastomers, thermoset elastomers, elastomeric composites, rigid polymers including polyphenylene, polyamide, polyimide, polyetherimide, polyethylene, epoxy, and their combinations.

In various embodiments, disclosed multi-diameter rods 100, 101 may be formed of a metallic material, e.g., a titanium alloy. In some embodiments, the multi-diameter rod may be formed of two or more materials. In one embodiment, elongated rod portions may be fabricated from carbon-reinforced PEEK and an intermediate section may be fabricated from PEEK. In another embodiment, elongated rod portions may be fabricated from PEEK and an intermediate section is fabricated from carbon-reinforced PEEK. It is envisioned that the longitudinal rod or device may be manufactured via various methods including machining, casting, injection-molding, insert-molding, overmolding, compression molding, transfer molding, co-extrusion, pultrusion, dip-coating, spray-coating, powder-coating, porous-coating, additive manufacturing, and their combinations. One skilled in the art, however, will realize that such materials and fabrication methods suitable for assembly and manufacture, in accordance with the present disclosure, would be appropriate.

With reference to FIGS. 1-5, a multi-diameter rod with eccentric centers 100 is configured for attachment to vertebrae during surgical treatment of a spinal disorder, examples of which are discussed herein. In various embodiments, multi-diameter rod 100 may include first longitudinal member portion 105 having a first end portion 106, a second longitudinal member portion 110 having a second end portion 111 opposite first end portion 106 and a transition portion 115 disposed therebetween. The transition portion 115 may join the first longitudinal member portion 105 to the second longitudinal member portion 110. In various embodiments, the first longitudinal member portion 105, transition portion 115, and the second longitudinal member portion 110 may be integrally formed as a single monolithic component or a unitary component by, e.g., a subtractive manufacturing process or a cast and mold process or by welding of parts together. A first longitudinal axis, A1 is defined between the first end portion 106 and the transition portion 115, and a second longitudinal axis A2 is defined between the second end portion 111 and the transition portion 115. In the example embodiment, longitudinal axis A1 extends through a center of first longitudinal member portion 105 in a lengthwise direction and longitudinal axis A2 extends through a center of second longitudinal member portion 110 in a lengthwise direction.

The length dimension of the first and second longitudinal member portions of the multi-diameter rod may be optimized depending on the intended surgical application and/or preference of a medical practitioner. It is understood that the medical practitioner may cut the multi-diameter rod to the proper length depending on the needs of the patient. In various embodiments, the length of the first longitudinal member portion 105 along axis A1 may be between about 270 mm to about 360 mm. In various embodiments, the length of the second longitudinal member portion 110 along axis A2 may be between about 150 mm to about 240 mm. In various embodiments, the ratio of lengths between the first longitudinal member portion 105 and the second longitudinal member portion 110 may be between about 1.125 and about 2.4. In some embodiments, the first longitudinal member portion 105 may be curved to more naturally follow the curvature of the human thoracic spine while the second longitudinal member portion 110 may be curved to more naturally follow the curvature of the human cervical spine.

Figure 3:
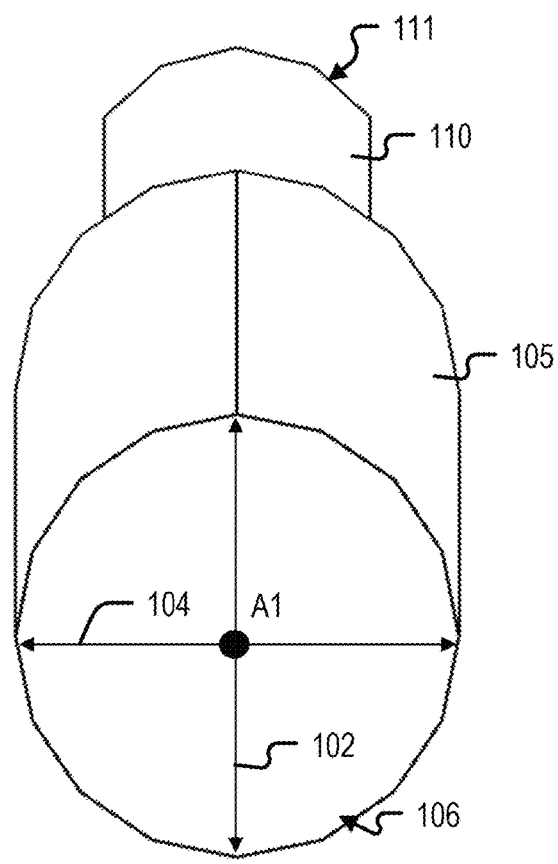
FIG. 3 depicts a perspective view of a first end portion of the spinal rod shown in in FIG. 1.
Figure 14:
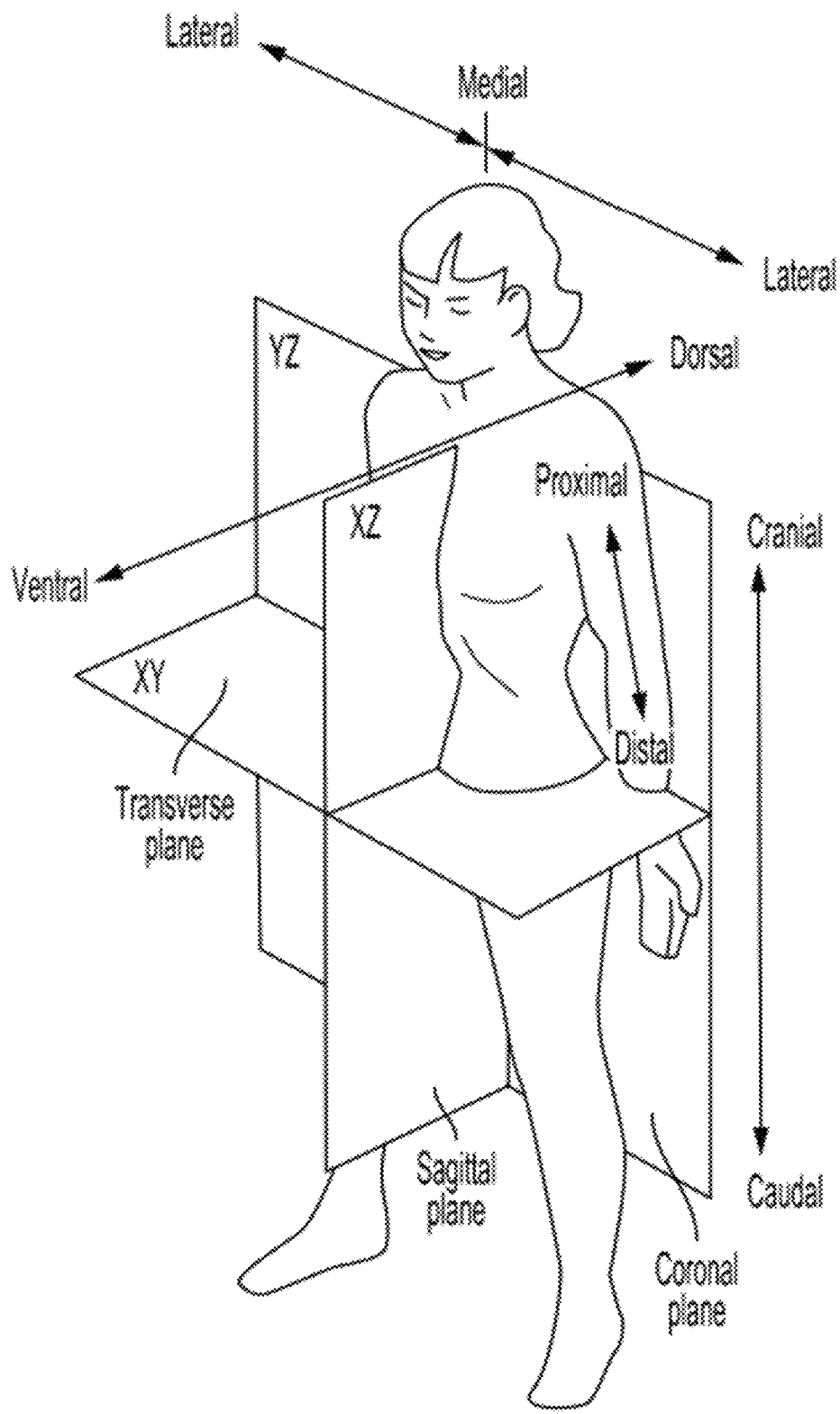
FIG. 14 depicts a reference diagram of the human spine.

First end portion 106 may have a generally circle, oval, and/or elliptical type geometry: In some embodiments, the shape may be generally cylindrical while also having flattened side surfaces such as, for example, an elongated shape resembling a pentagon and/or hexagon in cross-section. In these embodiments, a diameter, major diameter, and/or minor diameter may be understood as an approximation based on, for example, an imaginary circular and/or oval like shape that is circumscribed by and contacts portions of the perimeter of a cross section of the elongated shape. Numerous shapes are contemplated and disclosed herein, for example, oval, elliptical, D-shaped and/or oblong shapes that may include a major diameter and a minor diameter depending on the particular shape. As illustrated in FIG. 3, first end portion 106 may include a circle shape, oval shape, and/or cylindrical shape that generally represents and/or corresponds to a cross-sectional shape of the first longitudinal member portion 105. For example, a shape of first end portion 106 may correspond 1:1 with a cross section of the first longitudinal member portion 105. During use and/or installation, when viewed in a cross-section view; the first end portion may include a first major diameter 102 parallel to the sagittal plane of the patient's body (see FIG. 14). As illustrated, first end portion 106 also contains a first minor diameter 104 extending transverse to major diameter 102 and parallel to the transverse plane of the patient's body.

In various embodiments, the major diameter 102 of an oval shaped first end portion 106 may include any desired dimension depending upon the intended surgical application. In various embodiments, the major diameter 102 of the first end portion 106 may be between about 4.75 mm to about 6.35 mm. In various embodiments, the ratio between the major diameter 102 and the minor diameter 104 may be between about 1 and about 1.3.

Figure 4:
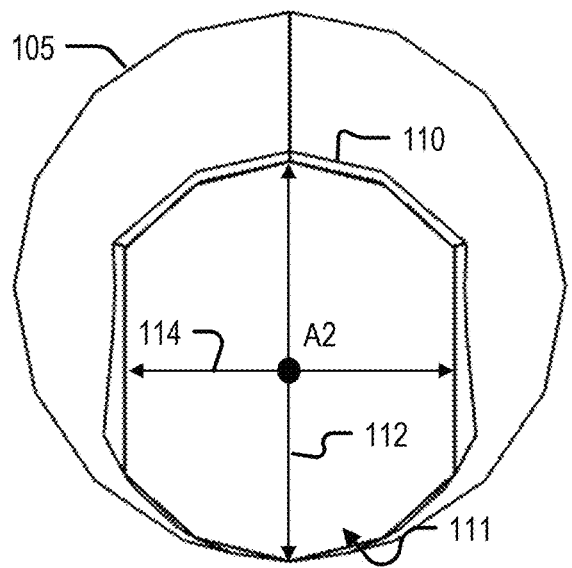
FIG. 4 depicts a perspective view of a second end portion of the spinal rod shown in in FIG. 1.

Second end portion 111 may have a generally circle, oval, and/or cylindrical geometry: In some embodiments, the shape may be generally cylindrical while also having flattened side surfaces such as e.g., an elongated shape resembling a pentagon and/or hexagon in cross-section. Numerous shapes are contemplated and disclosed herein, for example, oval, elliptical, and/or oblong shapes that may include a second major and a second minor diameter depending on the particular shape. As illustrated in FIG. 4, the second end portion 111 may include a circle shape, oval shape, and/or cylindrical shape that generally represents a cross-sectional shape of the second longitudinal member portion 110. During use and/or installation, when viewed in a cross-section view; the second end portion may have a second major diameter 112 that is parallel to the sagittal plane of the patient's body. The second end portion 111 may also contain a second minor diameter 114 extending transverse to major diameter 112 and parallel to the transverse plane of the patient's body.

In various embodiments, the major diameter 112 of an oval shaped second end portion 111 may include any desired dimension depending upon the intended surgical application. In various embodiments, major diameter 112 of the second end portion 112 may be between about 3 mm to about 4 mm. In various embodiments, the ratio between the major diameter 112 and the minor diameter 114 may be between about 1 and about 1.33.

Figure 5A:
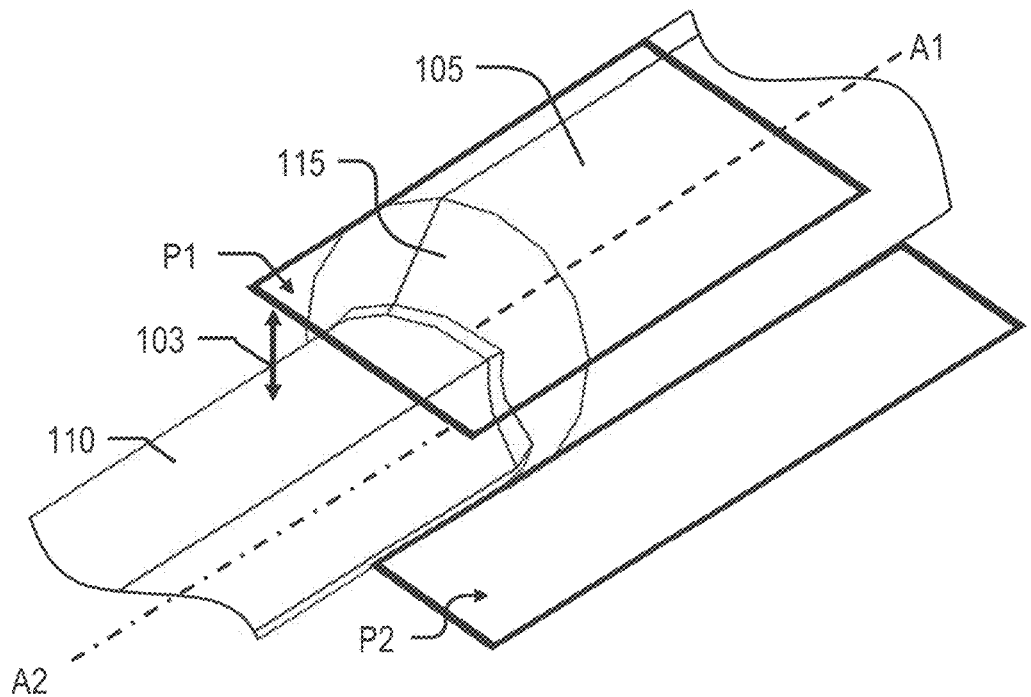
FIG. 5A depicts a first perspective view of various planes of the spinal rod shown in FIG. 1.
Figure 5B:
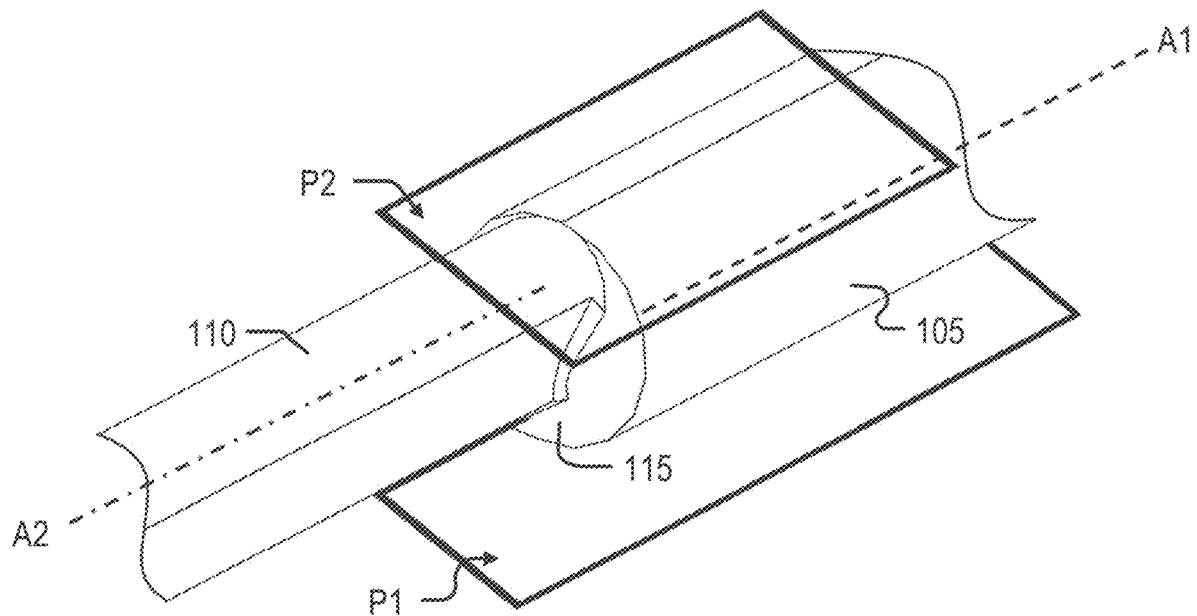
FIG. 5B depicts a second perspective view of various planes of the spinal rod shown in FIG. 1.
Figure 6:
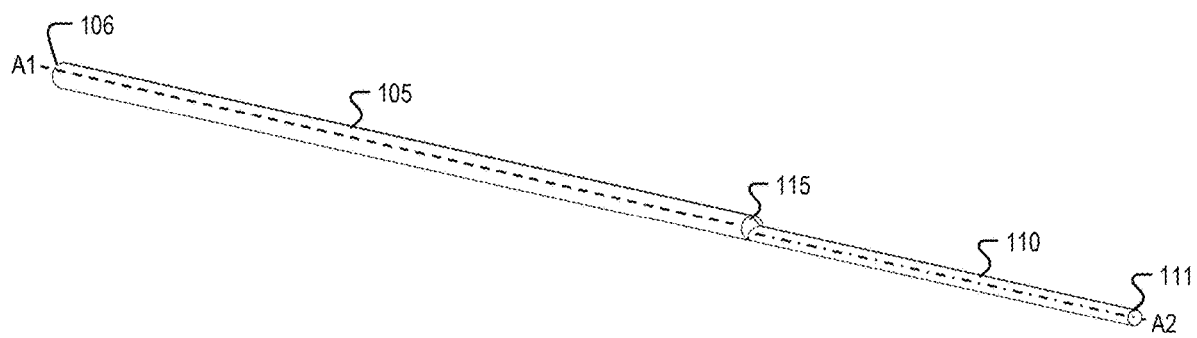
FIG. 6 depicts a perspective view of a second embodiment of the spinal rod in accordance with the principles of the present disclosure.
Figure 7A:
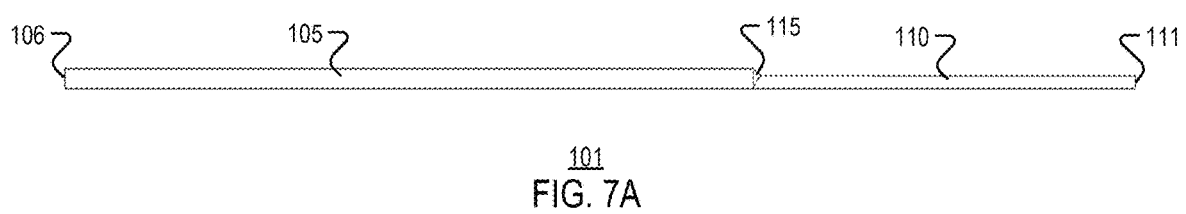
FIG. 7A depicts a side view of the spinal rod shown in FIG. 6.
Figure 7B:
FIG. 7B depicts a cross-sectional side view through the length of the spinal rod shown in FIG. 6.
Figure 8:
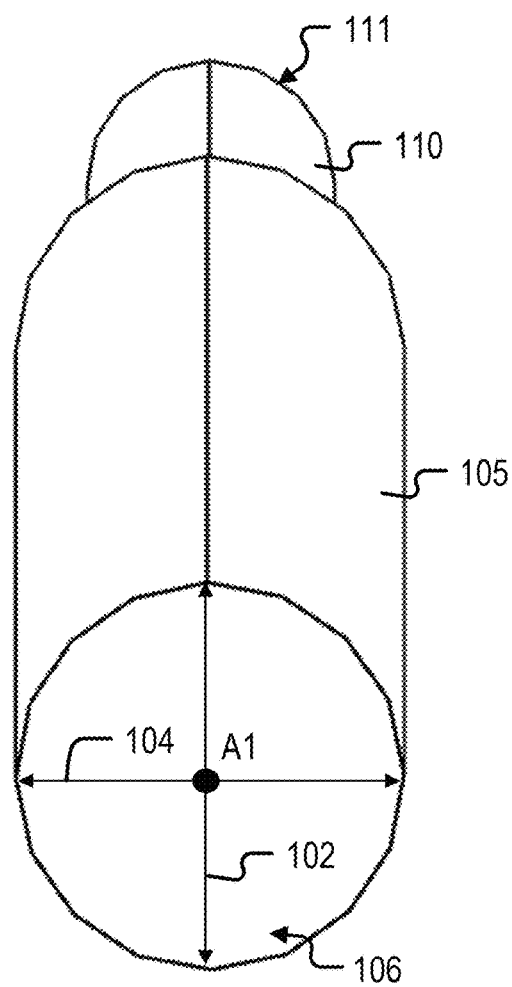
FIG. 8 depicts a perspective end view of a first end portion of the spinal rod shown in in FIG. 6.
Figure 9:
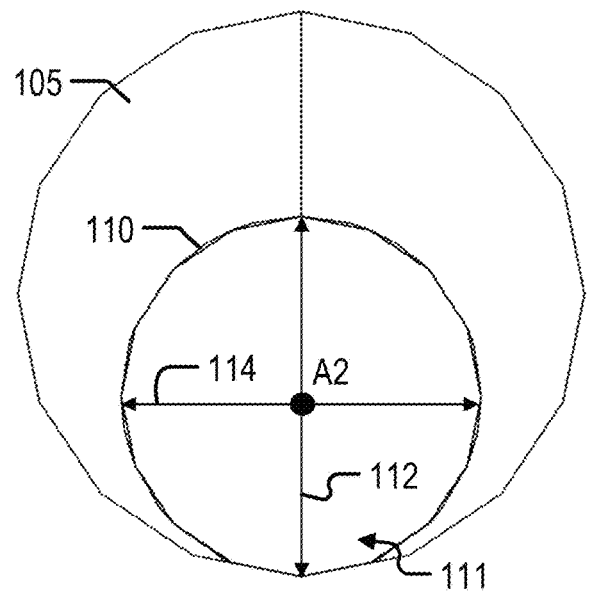
FIG. 9 depicts perspective end view of a second end portion of the spinal rod shown in in FIG. 6.
Figure 10:
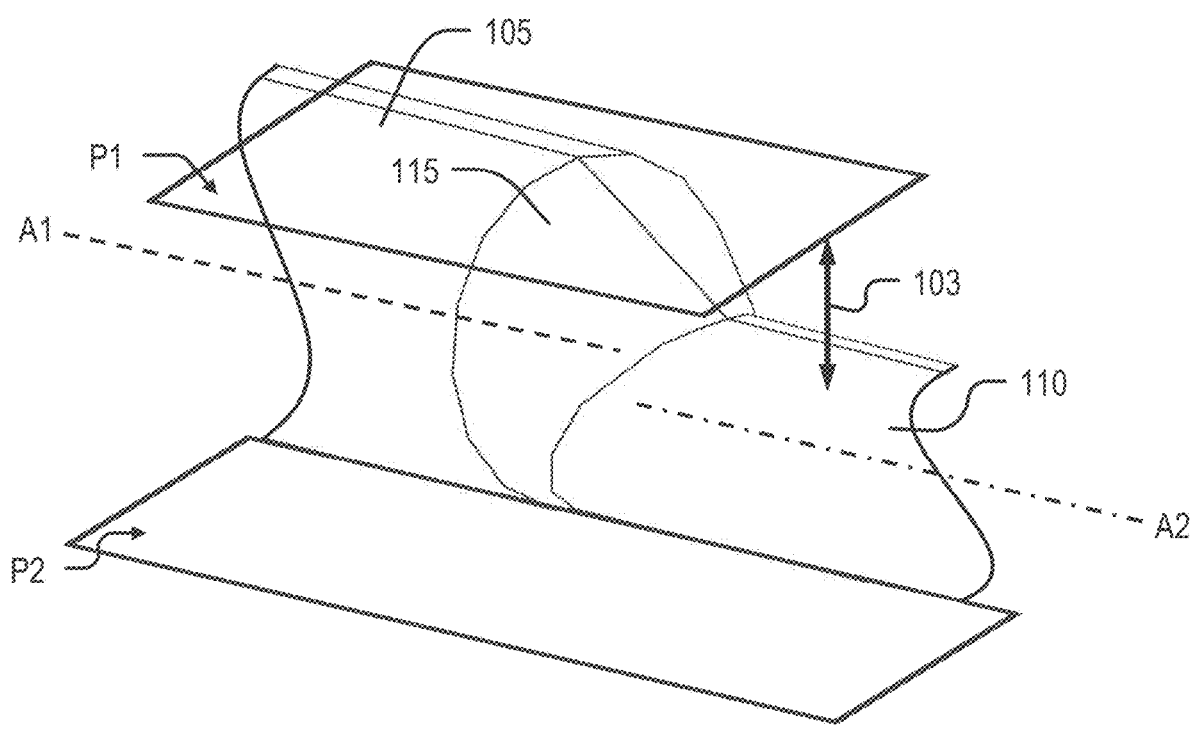
FIG. 10 depicts a perspective view of a transition portion of the spinal rod shown in FIG. 6.

As shown in FIG. 5A and FIG. 5B, longitudinal axes A1, A2 of the first and second longitudinal member portions 105, 110 are eccentric, i.e., they are not aligned and/or they are in a non-coaxial orientation with respect to one another. Additionally, in various embodiments, there may be an offset surface plane P1 where there is a height difference (e.g., gap distance 103) between the two members, and a co-extensive surface plane P2, where there is no height change (no relative gap distance) along the outside surface of the first and second longitudinal member portions 105 and 110. In the example embodiment, the gap distance 103 is attributable to a slope and length of the transition portion 115. The gap space 103 may range in dimension from about 0.75 mm to about 3.35 mm in a plane parallel to the face of first end portion 106. In the example embodiment, surface plane P2 may be understood as a plane that extends along and/or intersects an outermost surface of the first longitudinal member 105 and an outermost surface of the second longitudinal member 110. For example, plane P2 may be the only plane that can be drawn along a length of longitudinal rod 100 that touches both the outermost surface of first longitudinal member portion 105 and the outermost surface of second longitudinal member portion 110.

Referring generally to FIGS. 6-10, a second embodiment of a multi-diameter rod 101 having eccentric centers is disclosed. Multi-diameter rod 101 may have the same, similar, and/or substantially the same features and functionality as explained above with respect to rod 100. Accordingly, duplicative description will be omitted. In this embodiment, the first end portion 106 and second end portion 111 may have a circular shape. In various embodiments, the shape of the first end portion 106 may define and/or represent a cross-section view of the first longitudinal member portion 105 and the shape of the second end portion 111 may define and/or represent a cross-section view of the second longitudinal member portion 110. In the disclosed embodiment, the cross-section dimensions (thickness) of the first longitudinal member portion 105 remain consistent throughout a length thereof and the cross-section dimensions (thickness) of the second longitudinal member portion 110 remain consistent throughout a length thereof. In this way, the first member 105 may have a first consistent cross-section and the second member 110 may have a second consistent cross-section. Additionally, the transition portion 115 may be understood as the region of longitudinal rod 101 that transitions from the first cross-section to the second cross-section.

In various embodiments, the major diameter 112 of the second end portion 111 may have many dimensions depending upon the intended surgical application. In some embodiments, cross-sections of both the first end portion 106 and second end portion 111 may include a circular shape as depicted in the multi-diameter rod embodiment 101 shown in FIGS. 6-10. In the example embodiment, the shape of the cross-sections of a first end portion 106 and a second end portion 111 may resemble a perfect circle, e.g., a consistent cross-sectional shape resembling a perfect circle. In some embodiments, a diameter of the first end portion 106 and/or cross-section may be about 4.75 mm to about 6.35 mm. In various embodiments, a diameter of the second end portion 111 resembling a perfect circle, e.g., a consistent cross-sectional shape resembling a perfect circle, may be about 3 mm to about 4 mm.

In various embodiments, it is desirable for a multi-diameter rod 100, 101 with eccentric centers to exhibit variable major and minor diameters at the cross-section along the first and second longitudinal member portions 105 and 110 depending on the degree of the curvature of the spine. In some embodiments, the first longitudinal member portion 105 may have one consistent cross-section throughout the length as shown in the first end portion 106. In various embodiments, the second longitudinal member portion 110 may have one consistent cross-section throughout the length as shown in the second end portion 111. Accordingly, the major and minor diameters 112 and 114 of the cross-section of the second longitudinal member portion 110 may be optimized depending on the dorsal height difference of the spine.

While some embodiments may include increasing the major and minor diameters 112 and 114, another embodiment may reduce the major and minor diameters 112 and 114 to match the (i) contour of a particular patient's spine, e.g., differences in an adult patient's vs. a pediatric patient's and/or (ii) degree of the spine deformation/injury. In such an embodiment, an oval shaped cross-section second longitudinal member portion 110 may be used to provide more or less flexibility or reduce excess material and weight.

In some embodiments, multiple lengths may be contemplated at the transition portion 115 where a first longitudinal member portion 105 ends and the second longitudinal member portion 110 begins depending upon the intended surgical application. In some embodiments, when the dorsal height difference is large, the transition portion 115 may be reduced to allow for quick transition between the longitudinal member portions. In some embodiments, when the dorsal height is small, the transition portion 115 may be lengthened to provide a more gradual offset. In some embodiments, the length of the transition portion 115 may be between about 3 mm and about 5 mm, between about 5 mm and about 10 mm, or between about 10 mm and 20 mm. In some embodiments, the ratio of the length of the first longitudinal member portion 105 and the length of the transition portion 115 may be between about 54 and 120. In some embodiments, the ratio of the length of the second longitudinal member portion 110 and the length of the transition portion 115 may be between about 30 and about 80).

The multi-diameter rod 100, 101 described herein may be used with various bone anchors to secure the multi-diameter rod 100, 101 to boney anatomy of a patient, e.g., a pedicle portion of a vertebra of the human spine. As used herein, the term "bone anchor" shall broadly encompass any medically acceptable bone anchor, such as, for example, bone screws, pedicle screws, multi-axial screws (MAS), lateral mass screws, etc. that may be used in spinal surgery. For example, the multi diameter rod may be used in a multiple level procedure in which a plurality of pedicle screws or lateral mass screws is attached to each of the vertebrae C3 through T4, and the multi-diameter rod may span the cervico-thoracic junction as shown in FIGS. 11 and 12 without skipping a vertebrae. For example, and due in part to the co-extensive surface plane P2 provided by the eccentric centers of the multi-diameter rod 100, 101, the height difference between the second longitudinal member portion 110 in relation to the first longitudinal member portion 105 at the transition portion 115 allows stabilizing screws to be secured to each vertebra of the multiple level procedure without needing to skip a level.

In some embodiments, it is contemplated that the multi-diameter rod 100, 101 may be used with pedicle screws with an osteoconductive surface treatment or coated with an osteoconductive material, such as hydroxyapatite and/or osteoinductive agent, such as a bone morphogenic protein for enhanced bony fixation to facilitate motion of the treated spinal area. Multi-diameter rod 100, 101 with eccentric center may be made of radiolucent materials, such as polymers. Radiomarkers may be included for identification under x-ray, fluoroscopy, CT or other imaging techniques. Metallic or ceramic radiomarkers, such as tantalum beads, tantalum pins, titanium pins, titanium endcaps and platinum wires may be used, such as being disposed at the end portions of the longitudinal rod and/or along the length thereof.

In various embodiments, the multi-diameter rod 100, 101 may include markers, and or colors that allow the surgeon to easily identify the oval shaped first end and the oval or non-oval shaped second end for ease of implanting the longitudinal rod into the body.

In various embodiments, the first longitudinal member portion 105, second longitudinal member portion 110 and transition portion 115 may include an outer surface (not shown) that may include different surface treatments, such as textured, shot-peened, burnished, porous, patterned or wavy. In other embodiments the treated surface may further include a coating. The outer surface may be chemically treated or modified using various processes or materials which include oxidation, anodization, plasma treatment, vapor deposition, plating, coating or etching. It is contemplated that the vertebral rod may employ a heterogeneous composite having non-uniform carbon content.

In order to increase the estimated useful life of the elongated member, the outer surface may be treated to maintain fatigue resistance properties. For example, the outer surface may be work hardened by shot peening, followed by coating with an osteointegrating material as more specifically described in U.S. Patent Publication US2008/0221681 incorporated herein by reference as if set forth in full.

In some embodiments, the outer layer of the first longitudinal member portion 105, second longitudinal member portion 110 and transition portion 115 may include (not shown) a roughened surface and an osteintegrating coating disposed on the roughened surface. The surface texturing on the outer layer of the elongated member may improve the adhesion of the coating onto the surface of the elongated member. The coating not only increases osteointegration of the elongated member implant but also the resistance to fatigue.

In some embodiments the osteointegrating coating may be either osteoconductive or osteoinductive, or both. The osteointegrating material in the coating may be heterogeneous in some examples and homogeneous in others For example, in addition to, or in place of using HA (hydroxyapatite) as an osteoconductive coating, other exemplary osteoconductive coatings may include one or more of: biocompatible ceramics: calcium sulfate: a calcium phosphate such as HA, corraline hydroxyapatite, biphasic calcium phosphate, tricalcium phosphate, or fluorapatite: mineralized collagen: bioactive glasses: porous metals: bone particles; and demineralized bone matrix (DBM).

An osteoinductive coating may include: other forms of bone morphogenetic proteins (BMP), such as BMP-2, BMP-4, BMP-7, rhBMP-2, or rhBMP-7; demineralized bone matrix (DBM): transforming growth factors (TGF, e.g., TGF-β): osteoblast cells: growth and differentiation factor (GDF): insulin-like growth factor 1, platelet-derived growth factor, fibroblast growth factor, or any combination thereof.

In a further example, an osteoinductive coating material may include HMG-CoA reductase inhibitors, such as a member of the statin family, such as lovastatin, simvastatin, pravastatin, fluvastatin, atorvastatin, cerivastatin, mevastatin, pharmaceutically acceptable salts esters or lactones thereof, or any combination thereof. With regard to lovastatin, the substance nay be either the acid form or the lactone form or a combination of both.

In yet another example, an osteoinductive material may include LIM mineralized proteins (LMP), osteoinductive peptides, pharmaceutical agents such as antibiotics, pain medication, anti-inflammatory drugs, steroids, osteogenic compositions such as, therapeutic or infection resistant agent, or one or more of the previous in combination.

In some embodiments, the osteointegrating coating material may include multifunctional polymeric materials that inhibit adhesion and immune recognition between cells and tissue. These materials may include a tissue-binding component and a tissue non-binding component. Specific materials may include PEG/PLL copolymers with molecular weights greater than 300, with structures that include AB copolymers, ABA copolymers, and brush-type copolymers.

Additionally, the osteointegrating coating may use grafted polyionic copolymers that are able to attach to biological and non-biological samples to control cell-surface, cell-cell, and tissue-surface interactions. The coating may also include the application of polyionic, PEG-grafted copolymers.

In one embodiment, the osteointegrating coating may include grafted non-interactive material such as PEG (polyethylene glycol) or PEO (polyethylene oxide) within the polymer. Another example coating may be a combination polymer including a PEG-grafted poly(amino acid) with a polycationic backbone made of lysine, histidine, arginine or ornithine in D-, L-, or DL-configuration, or the polymer is a PEG-grafted polymer with a cationic backbone of a polysaccharide such as chitosan, partially deacetylated chitin, and amine-containing derivatives of neutral polysaccharides, or the polymer is a PEG-grafted non-peptide polyamine with a polycationic backbone such as poly(aminostyrene), poly(aminoacrylate), poly(N-methyl aminoacrylate), poly(N-ethylaminoacrylate), poly(N,N-dimethylaminoacrylate), poly(N,N-diethylaminoacrylate), poly (aminomethacrylate), poly(N-methyl amino-methacrylate), poly(N-ethyl aminomethacrylate), poly(N,N-dimethyl aminomethacrylate), poly(N,N-diethyl aminomethacrylate), poly(ethyleneimine), polymers of quaternary amines, such as poly(N,N, N-trimethylaminoacrylate chloride), poly (methacrylamidopropyltrimethyl ammonium chloride), or the polymer is a PEG-grafted charged synthetic polymer with a polycationic backbone such as polyethyleneimine, polyamino(meth)acrylate, polyaminostyrene, polyaminoethylene, poly(aminoethyl)ethylene, polyaminoethylstyrene, and N-alkyl derivatives thereof.

Other embodiments include one more coatings of a copolymer, including a PEG-grafted copolymer with an anionic backbone of a poly(amino acid) grafted with poly(ethylene glycol) where the amino acid contains an additional pendant carboxy group imparting a negative charge to the backbone at pH above 4 and in particular at neutral pH such as polyaspartic acid or polyglutamic acid: or a natural or unnatural polymer with pendant negatively charged groups, particularly carboxylate groups, including alginate, carrageenan, furcellaran, pectin, xanthan, hyaluronic acid, heparin, heparan sulfate, chondroitin sulfate, dermatan sulfate, dextran sulfate, poly(meth)acrylic acid, oxidized cellulose, carboxymethyl cellulose and crosmarmelose, synthetic polymers and copolymers containing pendant carboxyl groups, such as those containing maleic acid or fumaric acid in the backbone.

In yet another embodiment, the osteointegrating coating may include nanoparticles less than 500 nm in diameter. The nanoparticles act to reduce protein "denaturation" as well as subsequent foreign body reactions. Nanoparticles may include a metal particle, carbon particle, inorganic chemical particle, organic chemical particle, ceramic particle, graphite particle, polymer particle, protein particle, peptide particle, DNA particle, RNA particle, bacteria/virus particle, hydrogel particle, liquid particle or porous particle. Thus, the nanoparticles may be, for example, metal, carbon, graphite, polymer, protein, peptide, DNA/RNA, microorganisms (bacteria and viruses) and polyelectrolyte. Polymers may include copolymers of water-soluble polymers, including, but not limited to, dextran, derivatives of poly-methacrylamide, PEG, maleic acid, malic acid, and maleic acid anhydride and may include these polymers and a suitable coupling agent, including 1-ethyl-3(3-dimethylaminopropyl)-carbodiimide, also referred to as carbodiimide. Polymers may be degradable or nondegradable or of a polyelectrolyte material. Degradable polymer materials include poly-L-glycolic acid (PLGA), poly-DL-glycolic, poly-L-lactic acid (PLLA), PLLA-PLGA copolymers, poly(DL-lactide)-block-methoxy polyethylene glycol, polycaprolacton, poly (caprolacton)-block-methoxy polyethylene glycol (PCL-MePeg), poly(DL-lactide-co-caprolactone)-block-methoxy polyethylene glycol (PDLLACL-MePEG), some polysaccharide (e.g., hyaluronic acid, polyglycan, chitoson), proteins (e.g., fibrinogen, albumin, collagen, extracellular matrix), peptides (e.g., RGD, polyhistidine), nucleic acids (e.g., RNA, DNA, single or double stranded), viruses, bacteria, cells and cell fragments, organic or carbon-containing materials, as examples. Nondegradable materials include natural or synthetic polymeric materials (e.g., polystyrene, polypropylene, polyethylene teraphthalate, polyether urethane, polyvinyl chloride, silica, polydimethyl siloxane, acrylates, arcylamides, poly(vinylpyridine), polyacroleine, polyglutaraldehyde), some polysaccharides (e.g., hydroxypropyl cellulose, cellulose derivatives, DEXTRAN, dextrose, sucrose, FICOLL, PERCOLL, arabinogalactan, starch), and hydrogels (e.g., polyethylene glycol, ethylene vinyl acetate, N-isopropylacrylamide, polyamine, polyethyleneimine, poly-aluminum chloride).

Movement of the components of the multi-diameter rod between one and a plurality of orientations is contemplated and may include a range of increasing and decreasing levels of resistance of the components of the multi-diameter rod.

In assembly, operation and use, the multi-diameter rod is employed with a surgical procedure for treatment of a spinal disorder affecting a section of a spine of a patient, as discussed herein. The multi-diameter rod may also be employed with other surgical procedures. In particular, the multi-diameter rod is employed with a surgical procedure for treatment of a condition or injury of an affected section of the spine to provide stability for healing and therapeutic treatment, while allowing a desirable range of motion or load-sharing capability.

In use, to treat the affected section of the spine, a medical practitioner obtains access to a surgical site including vertebrea V in any appropriate manner, such as through incision and retraction of tissues. It is envisioned that the multi-diameter rod may be used in any existing surgical method or technique including open surgery, mini-open surgery, minimally invasive surgery and percutaneous surgical implantation, whereby the vertebra V is accessed through a mini-incision, or sleeve that provides a protected passageway to the area. Once access to the surgical site is obtained, a particular surgical procedure is performed for treating the spinal disorder. The multi-diameter rod is then employed to augment the surgical treatment. The multi-diameter rod may be delivered or implanted as a pre-assembled device or may be assembled in situ. The multi-diameter rod may be completely or partially revised, removed or replaced.

With reference to the installation shown in FIGS. 11 and 12, a method installation will now be disclosed. In use, a surgeon may install a multi-diameter rod 100, 101 with eccentric centers in a patient needing surgical treatment. For example, a surgeon may use any relevant embodiment in accordance with the principles of the disclosed multi-diameter rods 100, 101. The method may include the step of installing a first plurality of bone anchors, e.g., pedicle screws 205 that each include a connector portion for securing a longitudinal rod therein, e.g., multi-diameter rods 100, 101. The first plurality of pedicle screws 205 may be installed along a corresponding first plurality of vertebrae in the thoracic region of the spine along the first longitudinal member portion 105. The method may also include installing a second plurality of bone anchors, e.g., pedicle screws or lateral mass screws 210 that each include a connector portion for securing the longitudinal rod therein, e.g., multi-diameter rods 100, 101. The second plurality of pedicle screws or lateral mass screws 210 may be installed along a corresponding second plurality of vertebrae in the cervical region of the spine along the second longitudinal member portion 110. As seen in FIGS. 11 and 12, the first plurality of pedicle screws 205 installed in the thoracic vertebrae are relatively larger than the second plurality of pedicle screws or lateral mass screws 210 installed in the cervical vertebrae. This procedure may account for the vertebrae in the thoracic region being relatively large compared to the vertebrae in the cervical region of the spine. As seen best in the enlarged view of FIG. 12, it is shown that the multi-diameter rod 100, 101 having eccentric centers, may allow a surgeon to connect each vertebrae without skipping a level. For example, each vertebrae of the cervico-thoracic transition region of the spine is connected to the multi-diameter rod 100, 101 having eccentric centers.

The term "about" as used herein may be applied to modify any quantitative representation which could permissibly vary without resulting in a change in the basic function to which it is related. For example, the first end portions 106, as disclosed herein having a first major diameter 102 may permissibly have varying diameter within the scope of the invention while not materially affecting the function of the spinal rod.

It should be understood that various aspects disclosed herein may be combined in different combinations than the combinations specifically presented in the description and accompanying drawings. For example, features, functionality, and components from one embodiment may be combined with another embodiment and vice versa unless the context clearly indicates otherwise. Similarly, features, functionality, and components may be omitted unless the context clearly indicates otherwise. It should also be understood that, depending on the example, certain acts or events of any of the processes or methods described herein may be performed in a different sequence, may be added, merged, or left out altogether (e.g., all described acts or events may not be necessary to carry out the techniques).

Unless otherwise specifically defined herein, all terms are to be given their broadest possible interpretation including meanings implied from the specification as well as meanings understood by those skilled in the art and/or as defined in dictionaries, treatises, etc. It must also be noted that, as used in the specification and the appended claims, the singular forms "a," "an" and "the" include plural referents unless otherwise specified, and that the terms "comprises" and/or "comprising," when used in this specification, specify the presence of stated features, elements, and/or components, but do not preclude the presence or addition of one or more other features, steps, operations, elements, components, and/or groups thereof.

What is claimed is:

1. A spinal rod with multiple sections having eccentric centers, comprising:
    a first longitudinal portion extending along a first longitudinal axis and having a first cross-section and a first end portion, the first longitudinal axis extending lengthwise through a center of the first longitudinal portion;
    a second longitudinal portion extending along a second longitudinal axis having a second cross-section and a second end portion opposite the first end portion, the second longitudinal axis extending lengthwise through a center of the second longitudinal portion; and
    a transition portion adjoining the first longitudinal portion and the second longitudinal portion that is configured to transition from the first cross-section to the second cross-section,
    wherein the first longitudinal axis is offset with respect to the second longitudinal axis and the first longitudinal axis and the second longitudinal axis extend parallel with respect to one another,
    wherein a first bottom outside surface of the first longitudinal portion extending from the first end portion and towards the second end portion extends along a first co-extensive plane with a second bottom outside surface of the second longitudinal portion extending from the second end portion and towards the first end portion,
wherein the first bottom outside surface and the second bottom outside surface extend along the co-extensive plane at the same relative height,
wherein a first upper outside surface of the first longitudinal portion extending from the first end portion and towards the second end portion extends along a first upper plane with a second upper outside surface of the second longitudinal portion extending from the second end portion and towards the first end portion extends along a second upper plane,
wherein, in a side profile view, the first upper plane is vertically offset with respect to the second upper plane and the first upper plane and the second upper plane extend parallel with respect to one another, and
wherein a first end of the spinal rod comprises the first cross-section and a second end of the spinal rod opposite the first end of the spinal rod comprises the second cross-section.

2. The spinal rod of claim 1, wherein the spinal rod is a monolithic component and the first cross-section and the second cross-section each comprise an oval shape or a circular shape.

3. The spinal rod of claim 2, wherein the first cross-section of the first longitudinal portion comprises an oval shape having a major diameter and a minor diameter.

4. The spinal rod of claim 3, wherein the second cross-section of the second longitudinal portion comprises an oval shape having a major diameter and a minor diameter.

5. The spinal rod of claim 2, wherein the first cross-section of the first longitudinal portion comprises a circular shape having a consistent diameter.

6. The spinal rod of claim 5, wherein the second cross-section of the second longitudinal portion comprises a circular shape having a consistent diameter.

7. The spinal rod of claim 1, wherein the transition portion extends in the longitudinal direction for a distance that is within a range of about 3 mm to about 5 mm.

8. The spinal rod of claim 1, wherein a length of the first longitudinal portion is between about 270 mm and about 360 mm.

9. The spinal rod of claim 8, wherein a length of the second longitudinal portion is between about 150 mm and about 240 mm.

10. The spinal rod of claim 1, wherein:
the first longitudinal portion extends along the first longitudinal axis for a first distance and the second longitudinal portion extends along the second longitudinal axis for a second distance, and
a ratio of the first distance to the second distance is within a range of about 1.125 and 2.4.

11. The spinal rod of claim 1, wherein a major diameter of the first cross-section of the first longitudinal portion is between about 4.75 mm and about 6.35 mm.

12. The spinal rod of claim 11, wherein a major diameter of the second cross-section of the second longitudinal portion is between about 3 mm and about 4 mm.

13. The spinal rod of claim 11, wherein a minor diameter of the first cross-section of the first longitudinal portion is between about 4.75 mm and about 6.35.

14. The spinal rod of claim 13, wherein a minor diameter of the second cross-section of the first longitudinal portion is between about 3 mm and about 4 mm.

15. The spinal rod of claim 1, wherein:
the first cross-section of the first longitudinal portion comprises a first major diameter and a first minor diameter;
the second cross-section of the second longitudinal portion comprises a second major diameter and a second minor diameter;
a ratio of the first major diameter to the first minor diameter is within a range of about 1 to about 1.3;
a ratio of the second major diameter to the second minor diameter is within a range of 1 to about 1.33;
a ratio of the first major diameter to the second major diameter is within a range of about 1.18 to about 2.2; and
a ratio of the first minor diameter to the second minor diameter is within a range of about 1.18 to about 2.2.

16. The spinal rod of claim 1, wherein at least one of the first longitudinal portion and/or second longitudinal portion comprise an osteoconductive surface treatment, an osteoconductive coating, an osteoinductive coating, or a mixture thereof.

17. The spinal rod of claim 1, wherein the first longitudinal portion and the second longitudinal portion are separable components that are configured to be adjoined to one another.

18. A method for treating a plurality of vertebrae regions in a patient, the method comprising:
providing the spinal rod of claim 1;
attaching the spinal rod to a first plurality of bone anchors in the thoracic region of the spine and a second plurality of bone anchors in the cervical region of the spine; and
aligning the transition portion of the spinal rod above a cervico-thoracic junction such that the first longitudinal portion spans and supports the thoracic region of the spine and the second longitudinal portion spans and supports the cervical region of the spine.

19. A system including a spinal rod with multiple sections having eccentric centers, comprising:
a first plurality of bone anchors configured for attachment to the cervical spine;
a second plurality of bone anchors configured for attachment to the thoracic spine;
a first longitudinal portion extending along a first longitudinal axis and having a first cross-section and a first end portion, the first longitudinal axis extending lengthwise through a center of the first longitudinal portion;
a second longitudinal portion extending along a second longitudinal axis having a second cross-section and a second end portion opposite the first end portion, the second longitudinal axis extending lengthwise through a center of the second longitudinal portion; and
a transition portion adjoining the first longitudinal portion and the second longitudinal portion that is configured to transition from the first cross-section to the second cross-section,
wherein the first longitudinal axis is offset with respect to the second longitudinal axis and the first longitudinal axis and the second longitudinal axis extend parallel with respect to one another,
wherein a bottom first outside surface of the first longitudinal portion extending from the first end portion and towards the second end portion extends along a first co-extensive plane with a second bottom outside surface of the second longitudinal portion extending from the second end portion and towards the first end portion, wherein the first bottom outside surface and the second bottom outside surface extend along the co-extensive plane at the same relative height, wherein a first upper outside surface of the first longitudinal portion extending from the first end portion and towards the second end portion extends along a first upper plane with a second upper outside surface of the second longitudinal portion extending from the second end portion and towards the first end portion extends along a second upper plane, wherein, in a side profile view, the first upper plane is vertically offset with respect to the second upper plane and the first upper plane and the second upper plane extend parallel with respect to one another, wherein a first end of the spinal rod comprises the first cross-section and a second end of the spinal rod opposite the first end of the spinal rod comprises the second cross-section, and wherein the first longitudinal portion is configured to connect to the first plurality of bone anchors and the second longitudinal portion is configured to connect to the second plurality of bone anchors such that each vertebrae adjacent the transition portion is connected to the spinal rod.

20. The system of claim 19, wherein the first cross-section and the second cross-section each comprise an oval shape or a circular shape.

\* \* \* \* \*